(12) United States Patent
Abe et al.

(10) Patent No.: US 9,387,175 B2
(45) Date of Patent: Jul. 12, 2016

(54) AGENT FOR EVADING IMMUNE RESPONSE

(75) Inventors: Keietsu Abe, Sendai (JP); Kazuyoshi Kawakami, Sendai (JP); Tadafumi Ajiri, Sendai (JP); Manabu Fukumoto, Sendai (JP); Seiichi Takami, Sendai (JP); Takanari Togashi, Sendai (JP); Kimihide Muragaki, Sendai (JP); Toru Takahashi, Sendai (JP)

(73) Assignee: TOHOKU UNIVERSITY, Miyagi (JP)

( * ) Notice: Subject to any disclaimer, the term of this patent is extended or adjusted under 35 U.S.C. 154(b) by 142 days.

(21) Appl. No.: 14/238,616

(22) PCT Filed: Aug. 3, 2012

(86) PCT No.: PCT/JP2012/069800

§ 371 (c)(1),
(2), (4) Date: Jul. 3, 2014

(87) PCT Pub. No.: WO2013/024710

PCT Pub. Date: Feb. 21, 2013

(65) Prior Publication Data

US 2014/0314859 A1 Oct. 23, 2014

(30) Foreign Application Priority Data

Aug. 12, 2011 (JP) ................................ 2011-176686

(51) Int. Cl.

| | |
|---|---|
| *A61K 38/16* | (2006.01) |
| *A61K 9/16* | (2006.01) |
| *C01G 49/08* | (2006.01) |
| *C09C 1/24* | (2006.01) |
| *A61K 49/18* | (2006.01) |
| *B82Y 5/00* | (2011.01) |
| *B82Y 40/00* | (2011.01) |
| *B22F 1/00* | (2006.01) |
| *B82Y 30/00* | (2011.01) |

(52) U.S. Cl.

CPC ............. *A61K 9/1676* (2013.01); *A61K 38/168* (2013.01); *A61K 49/1863* (2013.01); *B22F 1/0018* (2013.01); *B22F 1/0062* (2013.01); *B82Y 5/00* (2013.01); *B82Y 30/00* (2013.01); *B82Y 40/00* (2013.01); *C01G 49/08* (2013.01); *C09C 1/24* (2013.01); *C01P 2004/62* (2013.01); *C01P 2006/12* (2013.01)

(58) Field of Classification Search

None

See application file for complete search history.

(56) References Cited

U.S. PATENT DOCUMENTS 5,433,878 A 7/1995 Arai et al.
5,635,154 A 6/1997 Arai et al.
2014/0314859 A1* 10/2014 Abe ...................... C01G 49/08 424/491

FOREIGN PATENT DOCUMENTS

| | | |
|---|---|---|
| JP | A-4-50105 | 2/1992 |
| JP | A-6-302421 | 10/1994 |
| JP | A-2005-21724 | 1/2005 |
| JP | A-2005-194148 | 7/2005 |
| JP | A-2008-162864 | 7/2008 |
| JP | A-2008-260724 | 10/2008 |
| JP | A-2012-111694 | 6/2012 |

OTHER PUBLICATIONS

Maeda et al, "Development of a cost-effective biodegradable plastic recycling system using the filamentous fungus *Aspergillus oryzae*", Baiosaiensu to Indasutori (2005), 63(4), 241-245, (abstract only).*
Tanaka et al, Bioscience, Biotechnology, and Biochemistry, 2014, vol. 78, No. 10, 1693-1699.*
De et al., "Application of Nanoparticles in Biology," *Advanced Materials*, 2008, vol. 20, pp. 4225-4241.
Jun et al., "Chemical Design of Nanoparticle Probes for High-Performance Magnetic Resonance Imaging," *Angewandte Chemie Int. Ed.*, 2008, vol. 47, pp. 5122-5135.
Kim et al., "Multifunctional Nanostructured Materials for Multimodal Imaging, and Simultaneous Imaging and Therapy," *Chemical Society Reviews*, 2009, vol. 38, pp. 372-390.
Shubayev et al., "Magnetic Nanoparticles for Theragnostics," *Advanced Drug Delivery Reviews*, 2009, vol. 61, pp. 467-477.
Kreuter, "Nanoparticulate Systems for Brain Delivery of Drugs," *Advanced Drug Delivery Reviews*, 2001, vol. 47, pp. 65-81.
Nam et al., "Nanoparticle-Based Bio-Bar Codes for the Ultrasensitive Detection of Proteins," *Science*, 2003, vol. 301, pp. 1884-1886.
Ito et al., "Magnetite Nanoparticle-loaded Anti-HER2 Immunoliposomes for Combination of Antibody Therapy with Hyperthermia," *Cancer Letters*, 2004, vol. 212, pp. 167-175.
Ito et al., "Medical Application of Functionalized Magnetic Nanoparticles," *Journal of Bioscience and Bioengineering*, 2005, vol. 100, No. 1, pp. 1-11.
Wang et al., "A General Strategy for Nanocrystal Synthesis," *Nature*, 2005, vol. 437, pp. 121-124.
Liu et al., "Self-Assembled Monolayer Coatings on Nanosized Magnetic Particles Using 16-Mercaptohexadecanoic Acid," *Langmuir*, 1995, vol. 11, pp. 4617-4622.
Bourlinos et al., "Surface Modification of Ultrafine Magnetic Iron Oxide Particles," *Chemical Materials*, 2002, vol. 14, pp. 3226-3228.
Hong et al., "Surface PEGylation and Ligand Exchange Chemistry of FePt Nanoparticles for Biological Applications," *Chemical Materials*, 2005, vol. 17, pp. 4617-4621.
Kim et al., "Phosphine Oxide Polymer for Water-Soluble Nanoparticles," *Journal of American Chemical Society*, 2005, vol. 127, pp. 4556-4557.

(Continued)

*Primary Examiner* — Nita M Minnifield
(74) *Attorney, Agent, or Firm* — Oliff PLC

(57) ABSTRACT

It has been found that modification of surfaces of nanoparticles with a RolA protein decreases an immunostimulation activity of the nanoparticles on myeloid dendritic cells and also decreases phagocytosis of the nanoparticles by macrophages. The present invention provides nanoparticles being modified with a biological molecule and having an immune-response evasion function.

8 Claims, 7 Drawing Sheets

(56) References Cited

OTHER PUBLICATIONS

Yi et al., "Silica-Coated Nanocomposites of Magnetic Nanoparticles and Quantum Dots," *Journal of American Chemical Society*, 2005, vol. 127, pp. 4990-4991.

Kim et al., "Magnetomicelles: Composite Nanostructures from Magnetic Nanoparticles and Cross-linked Amphiphilic Block Copolymers," *Nano Letters*, 2005, vol. 5, No. 10, pp. 1987-1991.

Zhang et al., "Surface Modification of Superparamagnetic Magnetite Nanoparticles and their Intracellular Uptake," *Biomaterials*, 2002, vol. 23, pp. 1553-1561.

Corot et al., "Macrophage Imaging in Central Nervous System and in Carotid Atherosclerotic Plaque Using Ultrasmall Superparamagnetic Iron Oxide in Magnetic Resonance Imaging," *Investigative Radiology*, 2004, vol. 39, No. 10, pp. 619-625.

Neuberger et al., "Superparamagnetic Nanoparticles of Biomedical Applications: Possibilities and Limitations of a New Drug Delivery System," *Journal of Magnetism and Magnetic Materials*, 2005, vol. 293, pp. 483-496.

Nikolic et al., "Tailor-Made Ligands for Biocompatible Nanoparticles," *Angewandte Chemie Int. Ed.*, 2006, vol. 45, pp. 6577-6580.

Thünemann et al., "Maghemite Nanoparticles Protectively Coated with Poly(ethylene imine) and Poly(ethylene oxide)-*block*-poly(glutamic acid)," *Langmuir*, 2006, vol. 22, pp. 2351-2357.

Bailey et al., "Core-Shell Semiconductor Nanocrystals for Biological Labeling," *The Chemistry of Nanomaterials: Synthesis, Properties and Application*, vol. 2, (Eds: C. N. R. Rao, A. Muller, A. K. Cheetham), Wiley-VCH, Weinheim, 2004, pp. 405.

Sun et al., "Magnetic Nanoparticles in MR Imaging and Drug Delivery," *Advanced Drug Delivery Reviews*, 2008, vol. 60, pp. 1252-1265.

Aimanianda et al., "Surface Hydrophobin Prevents Immune Recognition of Airborne Fungal Spores," *Nature*, 2009, vol. 460, No. 7259, pp. 1117-1121, with 18 pages of supporting information.

Kase et al., "Kojikin no Saibo Hyoso Tanpakushitsu Hydrophobin (HypA) no Tanryotai Seisan," *Japan Society for Bioscience, Biotechnology, and Agrochemistry Taikai Koen Yoshishu*, 2009, vol. 2009, p. 272.

Ishikawa et al., "Kojikin Aspergillus Oryzae no Saibo Hyoso Tanpakushitsu Hydrophobin-gun no Kyokuzai Kaiseki," *Japan Society for Bioscience, Biotechnology, and Agrochemistry Taikai Koen Yoshishu*, 2009, vol. 2009, p. 272.

Dagenais et al., "*Aspergillus fumigatus* LaeA-Mediated Phagocystosis is Associated with a Decreased Hydrophobin Layer," *Infection and Immunity*, 2010, vol. 78, No. 2, pp. 823-829.

Takahashi et al., "The Fungal Hydrophobin RoIA Recruits Polyesterase and Laterally Moves on Hydrophobic Surfaces," *Molecular Microbiology*, 2005, vol. 57, No. 6, pp. 1780-1796.

Wang et al., "Structural Changes and Molecular Interactions of Hydrophobin SC3 in Solution and on a Hydrophobic Surface," *Protein Science*, 2002, vol. 11, pp. 1172-1181.

International Search Report issued in International Application No. PCT/JP2012/069800 mailed Oct. 9, 2012.

International Preliminary Report on Patentability issued in International Application No. PCT/JP2012/069800 mailed Feb. 20, 2014.

\* cited by examiner

RolA

UNCOATED

COATED

SEQUENCE LISTING

```
<160> NUMBER OF SEQ ID NOS: 2

<210> SEQ ID NO 1
<211> LENGTH: 456
<212> TYPE: DNA
<213> ORGANISM: Aspergillus oryzae
<220> FEATURE:
<221> NAME/KEY: CDS
<222> LOCATION: (1)..(453)
<223> OTHER INFORMATION:

<400> SEQUENCE: 1
```

| | |
|---|---:|
| atg cag ttc tcc gtc gcc gct gtt ctt gct ctg gct act gcc gtt gcc<br>Met Gln Phe Ser Val Ala Ala Val Leu Ala Leu Ala Thr Ala Val Ala<br>1               5                   10                  15 | 48 |
| gct ctt cct cct gcc tct ggc act ggc gct ggc cag caa gtc gga cac<br>Ala Leu Pro Pro Ala Ser Gly Thr Gly Ala Gly Gln Gln Val Gly His<br>            20                  25                  30 | 96 |
| tcc aag aac gac ttc cct ctc cct aag gag ttg acc acc aag cag gcc<br>Ser Lys Asn Asp Phe Pro Leu Pro Lys Glu Leu Thr Thr Lys Gln Ala<br>        35                  40                  45 | 144 |
| gcc gac aag tgt ggt gac cag gct cag ctc acc tgc tgc aac aag acc<br>Ala Asp Lys Cys Gly Asp Gln Ala Gln Leu Thr Cys Cys Asn Lys Thr<br>    50                  55                  60 | 192 |
| gtc aag acc ggt gac ttc acc cag gtt gag gag ggt ctc ctt gct ggc<br>Val Lys Thr Gly Asp Phe Thr Gln Val Glu Glu Gly Leu Leu Ala Gly<br>65                  70                  75                  80 | 240 |
| ctc ctc tcc aac ctc ctc ggt gcc gga cag ggc tcc cag ggt ctt ggt<br>Leu Leu Ser Asn Leu Leu Gly Ala Gly Gln Gly Ser Gln Gly Leu Gly<br>                85                  90                  95 | 288 |
| ctc ttg gat gag tgc acc aac atc cct gtt atc ccc atc atc tcc atc<br>Leu Leu Asp Glu Cys Thr Asn Ile Pro Val Ile Pro Ile Ile Ser Ile<br>            100                 105                 110 | 336 |
| gcc tct cct cag gag aag tgc aag cag ccc atc tct tgc tgc cag aac<br>Ala Ser Pro Gln Glu Lys Cys Lys Gln Pro Ile Ser Cys Cys Gln Asn<br>        115                 120                 125 | 384 |
| acc aag tcc agc gcc gat ggc gac ctc gtc ggt att ggt ctt cct tgc<br>Thr Lys Ser Ser Ala Asp Gly Asp Leu Val Gly Ile Gly Leu Pro Cys<br>    130                 135                 140 | 432 |
| atc gct ctc ggc tct ctc ctg taa<br>Ile Ala Leu Gly Ser Leu Leu<br>145                 150 | 456 |

<210> SEQ ID NO 2
<211> LENGTH: 151
<212> TYPE: PRT
<213> ORGANISM: Aspergillus oryzae

<400> SEQUENCE: 2

Met Gln Phe Ser Val Ala Ala Val Leu Ala Leu Ala Thr Ala Val Ala
1               5                   10                  15

Ala Leu Pro Pro Ala Ser Gly Thr Gly Ala Gly Gln Gln Val Gly His
            20                  25                  30

Ser Lys Asn Asp Phe Pro Leu Pro Lys Glu Leu Thr Thr Lys Gln Ala
        35                  40                  45

Ala Asp Lys Cys Gly Asp Gln Ala Gln Leu Thr Cys Cys Asn Lys Thr
    50                  55                  60

Val Lys Thr Gly Asp Phe Thr Gln Val Glu Glu Gly Leu Leu Ala Gly
65                  70                  75                  80

Leu Leu Ser Asn Leu Leu Gly Ala Gly Gln Gly Ser Gln Gly Leu Gly
                85                  90                  95

Leu Leu Asp Glu Cys Thr Asn Ile Pro Val Ile Pro Ile Ile Ser Ile
            100                 105                 110

Ala Ser Pro Gln Glu Lys Cys Lys Gln Pro Ile Ser Cys Cys Gln Asn
        115                 120                 125

Thr Lys Ser Ser Ala Asp Gly Asp Leu Val Gly Ile Gly Leu Pro Cys
    130                 135                 140

Ile Ala Leu Gly Ser Leu Leu
145                 150

AGENT FOR EVADING IMMUNE RESPONSE

TECHNICAL FIELD

The present invention relates to an agent for evading immune response, comprising a RolA protein.

BACKGROUND ART

Nanometer-sized ultrafine particles containing a metal element as a constituent element (for example, metal oxide nanoparticles and metal hydroxide nanoparticles) are expected to be used in the wide fields of catalysts, storage materials, light-emitting materials, fluorescent materials, secondary battery materials, electronic component materials, magnetic recording materials, polishing materials, optoelectronics, pharmaceuticals, cosmetics, and the like. It is known that materials using nanometer-sized particles often exhibit interesting characteristics attributable to the extremely small sizes. Reportedly, some of engineering, electronic, mechanical, and chemical characteristics exhibited by these materials are different from those of already-existing bulk materials. In particular, magnetic nanoparticles have attracted increasing attention, and are started to be researched actively. Notable and attractive properties among characteristics exhibited by metal element-containing nanoparticles including magnetic nanoparticles are closely related with quantum properties and magneto-optical property, and have attracted industrial and scientific attention in the wide applications. Magnetic nanoparticles are expected to find many applications such as ferrofluids, high-density recording materials, and medical diagnostic materials.

Since magnetic nanoparticles have promising applications, magnetic nanoparticles have attracted increasing attention from researchers in wide fields (NPLs 1 to 4). Magnetite (magnetic iron ore, $Fe_3O_4$) is chemically nontoxic to the human. Hence, a lot of medical applications of $Fe_3O_4$ have been proposed, and $Fe_3O_4$ is being researched for those medical applications. The proposed medical applications include, for example, an application as a carrier for drug or gene delivery, an application in hyperthermia therapy of cancer, applications in biosensors, and applications in the tissue engineering including regeneration and transplantation medicine (NPLs 5 to 8).

To achieve such medical applications, $Fe_3O_4$ is required to be sufficiently small, and be dispersed well in water or blood, without aggregation. In addition, $Fe_3O_4$ is required to evade capture by phagocytes including macrophages, i.e., to be stealthy to immunological reactions in the human body. $Fe_3O_4$ nanoparticles are synthesized by various methods (NPL 9), and surface properties of $Fe_3O_4$ nanoparticles can be altered by several approaches including the ligand exchange method (NPLs 10 to 15)

To evade the capture by phagocytes and extend the half-life in blood (NPL 16), coating iron oxide nanoparticles with various polymers such as polyethylene glycol has been attempted (NPLs 17 to 20). However, these methods are each practically difficult to apply, and have a problem associated with the stability of a dispersion during transfer between solvents (NPL 21).

In addition, nanoparticles greater than 200 nm are reported to be captured by phagocytes in the spleen (NPL 22).

Note that the group of the present inventors has developed a technology using a hydrothermal synthesis system under high-temperature and high-pressure water such as subcritical water or supercritical water as an approach for synthesizing metal oxide nanoparticles or metal hydroxide nanoparticles (PTLs 1 to 5).

CITATION LIST

Patent Literature

[PTL 1] Japanese Unexamined Patent Application Publication No. Hei 4-50105
[PTL 2] Japanese Unexamined Patent Application Publication No. Hei 6-302421
[PTL 3] Japanese Unexamined Patent Application Publication No. 2005-21724
[PTL 4] Japanese Unexamined Patent Application Publication No. 2005-194148
[PTL 5] Japanese Unexamined Patent Application Publication No. 2008-162864

Non Patent Literature

[NPL 1] M. De, P. S. Ghosh, V. M. Rotello, Adv. Mater. 2008, 20, 4225-4241
[NPL 2] Y. Jun, J. H. Lee, J. Cheon, Angew. Chem. Int. Ed. 2008, 47, 5122-5135
[NPL 3] J. Kim, Y. Piao, T. Hyeon, Chem. Soc. Rev. 2009, 38, 372-390
[NPL 4] V. I. Shubayev, T. R. Piasanic, S. Jin, Advanced Drug Delivery Review 2009, 61, 467-477
[NPL 5] J. Kreuter, Adv. Drug. Deliv. Rev. 2001, 47, 65-81
[NPL 6] J. M. Nam, C. S. Thaxton, D. A. Mirkin, Science 2003, 301, 1884-1886
[NPL 7] A. Ito, Y. Kuga, H. Honda, H. Kikkawa, A. Horiuchi, Y. Watanabe, T. Kobayashi, Cancer Lett. 2004, 212, 167-175
[NPL 8] A. Ito, M. Shinlai, H. Honda, T. Kobayashi, J. Biosci. Bioeng. 2005, 100, 1-11
[NPL 9] X. Wang, J. Zhuang, Q. Peng, Y. Li, Nature 2005, 437, 121-124
[NPL 10] Q. Liu, Z. Xu, Langmuir, 1995, 11, 4617-4622
[NPL 11] A. B. Bourlinos, A. Bakandritos, V. Georgakilas, D. Petridis, Chem. Mater. 2002, 14, 3226-3228
[NPL 12] R. Hong, N, O. Fischer, T. Emrick, V. M. Rotello, Chem. Mater. 2005, 17, 4617-4621
[NPL 13] S.-W. Kim, S. Kim, J. B. Tracy, A. Jasanoff, M. G. Bawendi, J. Am. Chem. Soc. 2005, 127, 4556-4557
[NPL 14] D. K. Yi, S. T. Selvan, S. S. Lee, G. C. Papaefthymiou, D. Kundaliya, J. Y. Ying, J. Am. Chem. Soc. 2005, 127, 4990-4991
[NPL 15] B.-S. Kim, J.-M. Qiu, J.-P. Wang, T. A. Taton, Nano Lett. 2005, 5, 1987-1991
[NPL 16] Y. Zhang, N. Kohler, M. Zhang, Biomaterials 2002, 23, 1553-1560
[NPL 17] C. Corot, K. G. Petry, R. Trivedi, A. Saleh, C. Jonkmanns, J. F. Le Bas, E. Blezer, M. Rausch, B. Brochet, P. Foster-Gareau, D. Balériaux, S. Gaillard, V. Dousset, Invest Radiol. 2004, 39, 619-625
[NPL 18] T. Neuberger, B. Schopf, H. Hofmann, M. Hofmann, B. Rechenberg, J. Magn. Magn. Mater. 2005, 293, 483-496
[NPL 19] M. S, Nikolic, M. Krack, V. Aleksandrovic, A. Kornowski, S. Forster, H. Weller, Angew. Chem. Int. Ed. 2006, 45, 6557-6580
[NPL 20] A. F. Thunemann, D. Schutt, L. Kaufner, U. Pison, H. Mohwald, Langmuir 2006, 22, 2351-2357

[NPL 21] R. E. Bailey, S, Nie, in The Chemistry of Nanomaterials: Synthesis, Properties and Application (Eds: C. N. R. Rao, A. Muller, A. K. Cheetham), WILEY-VCH, Weinheim, 2004, pp. 405

[NPL 22] C. Sun, J. S. H. Lee, M. Zhang, Advanced Drug Delivery Reviews 2008, 60, 1252-1265

[NPL 23] V. Aimanianda, J. Bayry, S. Bozza, O. Kniemeyer, K. Perruccio, S R. Elluru, C. Clavaud, S. Paris, A A. Brakhage, S V. Kaveri, L. Romani, J P. Latge. Nature. 2009, Aug. 27; 460(7259), 1117-1121.

SUMMARY OF INVENTION

Technical Problem

As described above, development of various nanoparticles provided with an immune-response evasion function has been attempted. However, in the cases of medical applications and the like, increased safety is required, while an immune-response evasion function is provided. Here, the technology is preferably so highly versatile that an immune-response evasion function can be provided not only to extremely small-sized nanoparticles but also to nanoparticles having diameters of 200 nm or more. In this respect, it is required that a molecule having an excellent immune-response evasion function be identified among biological molecules, and nanoparticles modified with the molecule be developed.

The present invention has been made under such circumstances, and an object of the present invention is to provide nanoparticles having an immune-response evasion function and being modified with a biological molecule.

Solution to Problem

The present inventors have made earnest studies to achieve the above object. As a result, the present inventors have found that modification of the surfaces of nanoparticles ($Fe_3O_4$ modified with catechol) with a RolA (RodA like protein A) protein originated from a filamentous fungus of the genus *Aspergillus* decreases the immunostimulation activity of the nanoparticles on myeloid dendritic cells and decreases phagocytosis of the nanoparticles by macrophages. In particular, it is astonishing that nanoparticles having diameters of 200 nm or more, which have been thought to be unable to evade the phagocytosis by macrophages so far, can evade the phagocytosis by macrophages, when modified with a RolA protein. The nanoparticles modified with a RolA protein originated from a Koji mold used for producing various foods such as sake, soybean paste, and soy sauce or originated from a highly safe microorganism other than Koji molds have both the excellent immune-response evasion function as described above and a high safety, and are useful as a composition for medical applications or the like.

More specifically, the present invention provides the following invention.

(1) A composition for evading immune response, comprising a RolA protein.

(2) The composition according to (1), wherein the RolA protein is originated from a filamentous fungus of the genus *Aspergillus*.

(3) The composition according to (1) or (2), further comprising a nanometer-sized metal simple substance or a nanometer-sized metal compound.

(4) The composition according to (3), wherein a surface of the nanometer-sized metal simple substance or the nanometer-sized metal compound is modified with the RolA protein.

(5) The composition according to (4), wherein the nanometer-sized metal simple substance or the nanometer-sized metal compound is modified with catechol.

(6) The composition according to any one of (1) to (5), wherein the evasion of immune response includes avoidance of immunostimulation on a dendritic cell and evasion of phagocytosis by a macrophage.

Advantageous Effects of Invention

Nanoparticles for medical applications present a big problem of being captured by the immune system in injection into a human or an animal. It has been known so far that a RodA protein originated from *Aspergillus* fumigates does not stimulate dendritic cells (NPL 23), but it is not known whether the RodA protein has a function of evading the phagocytosis by macrophages. In addition, *Aspergillus* fumigates is a causative microorganism of aspergillosis, and hence the use of a molecule originated from *Aspergillus* fumigates may cause a safety problem.

The composition of the present invention is nanoparticles obtained by coating, with a RolA protein, a metal simple substance or a metal compound stable in living organisms. The composition of the present invention has such an excellent immune-response evasion function (stealth function) that the composition of the present invention does not stimulate dendritic cells, and evades phagocytosis by macrophages. In addition, the composition of the present invention uses a RolA protein originated from a Koji mold or the like, and hence is highly safe. Moreover, the RolA protein used in the composition of the present invention can provide the immune-response evasion function also to nanoparticles having diameters of 200 nm. Moreover, the RolA protein has the immune-response evasion function even at a high concentration of 50 μg/ml. Accordingly, the present invention provides nanoparticles having both an excellent immune-response evasion function and a high safety.

DESCRIPTION OF EMBODIMENTS

The present invention provides a composition for evading immune response, comprising a RolA protein.

In the present invention, "evading immune response" means that, when injected into a human or animal body, the composition exhibits a function of evading capture by the immune system. Here, the meaning of the "evade" include complete evasion of the capture and also significant decrease of the capture. The evading immune response specifically means that the composition avoids stimulating cells involved in the immune system such as dendritic cells (for example, myeloid dendritic cells), macrophages, T lymphocytes including Helper T cells, killer T cells, Regulatory T cells, Natural killer T cells, and the like, B lymphocytes, natural killer cells, monocytes, Kupffer cells, microglial cells, Langerhans cells, neutrophils, eosinophils, basophils, and mast cells.

The stimulation on cells involved in the immune system may be an action to stimulate an intracellular signal transduction pathway mediated by a pattern recognition receptor expressed in these cells involved in the immune system, an action to produce a cytokine or a chemokine and/or an action to stimulate a production system of a cytokine or a chemokine, an action to express a co-stimulatory molecule and/or an action to stimulate expression of a co-stimulatory molecule, or an action to express an adhesion molecule and/or an action to stimulate expression of an adhesion molecule. Examples of the cytokine and the chemokine include IL-12 and TNF-α.

In addition, the capture by the immune system includes foreign substance elimination actions mediated by the reticuloendothelial system, for example, a phagocytosis action in which macrophages are involved.

The origin of the "RolA protein" used for the composition of the present invention is not particularly limited. Preferably, the "RolA protein" is a RolA protein originated from a microorganism which is applied in the field of foods and the like and which has a high safety. The microorganism is preferably a filamentous fungus of the genus *Aspergillus*, and particularly preferably a Koji mold. Examples of the Koji mold include *Aspergillus oryzae* and *Aspergillus niger*.

In the present invention, the "RolAprotein" includes recombinant proteins expressed from RolA genes, purified RolA proteins, and natural or artificial variants of these proteins.

A typical amino acid sequence of the RolA protein from *Aspergillus oryzae* is shown in SEQ ID NO: 2, and a typical base sequence of a DNA coding the protein is shown in SEQ ID NO: 1 (see GenBank Accession No: AB094496.1). In SEQ ID NO: 2, the amino acid sequence from the 1 to 16 positions is a signal sequence. In the present invention, a protein from which the signal sequence is removed can be used. In the present invention, it is also possible to use a natural or artificial variant of the RolA protein originated from *Aspergillus oryzae*, in addition to the RolA protein originated from *Aspergillus oryzae*. Moreover, RolA proteins originated from other living organisms and natural or artificial variants thereof can also be used.

A mode of the protein other than the RolA protein from *Aspergillus oryzae* is a protein having an amino acid sequence which is the same as the amino acid sequence shown in SEQ ID NO: 2, except that one or multiple amino acids are substituted, deleted, added, and/or inserted, and having the above-described immune response evasion function. Here, the term "multiple" means a number of amino acids in a range where the immunity evasion function is retained, and is generally a number of mutations of amino acids which is about the same as the number of mutations of amino acids occurring in a well-known method such as the site-directed mutagenesis method or occurring naturally. Specifically, the "multiple" is generally 1 to 30, preferably 1 to 10, more preferably 1 to 5, and most preferably 1 to 2.

Another mode of the protein other than the RolA protein originated from *Aspergillus oryzae* is a protein being coded by a DNA which hybridizes with a DNA having the base sequence shown in SEQ ID NO: 1 under stringent conditions, and having the above-described immune response evasion function. Examples of the stringent hybridization conditions include conditions of 6 M urea, 0.4% SDS, and 0.5×SSC, and hybridization conditions with a similar stringency. When conditions with a higher stringency, for example, conditions of 6 M urea, 0.4% SDS, and 0.5×SSC, are employed, isolation of a DNA having a higher homology can be expected.

Still another mode of the protein other than the RolA protein originated from *Aspergillus oryzae* is a protein having an amino acid sequence having a homology not less than 80% (for example, not less than 85%, 90%, 95%, 97%, or 99%) to the amino acid sequence shown in SEQ ID NO: 2 and having the above-described immune response evasion function. The homology of a sequence can be determined by using the program of BLASTX (amino acid level) (Altschul et al. Mol. Biol., 1990, 215, 403-410). This program is based on the algorithm BLAST of Karlin and Altschul (Proc. Natl. Acad. Sci. USA, 1990, 87, 2264-2268, and Proc. Natl. Acad. Sci. USA, 1993, 90, 5873-5877). When an amino acid sequence is analyzed by BLASTX, the parameters are, for example, as follows: score=50, and wordlength=3. Meanwhile, when an amino acid sequence is analyzed by using the Gapped BLAST program, the analysis can be conducted as described in Altschul et al. (Nucleic Acids Res. 1997, 25, 3389-3402). When BLAST and Gapped BLAST programs are used, default parameters of the programs are used. Specific approaches of these analytic methods are known.

The composition of the present invention can further comprise a nanometer-sized (not less than 1 nm and less than 1 μm) metal simple substance or metal compound. In this case, a surface of the metal simple substance or the metal compound is preferably modified with the RolA protein. Thus, when the composition is administered to a living organism, it is possible to effectively evade the immune response due to the metal simple substance or the metal compound. When modified with a RolA protein, even a metal simple substance or a metal compound of 200 nm or more can evade the immune response.

The metal compound is not particularly limited, as long as nanoparticles can be formed. Examples of the metal compound include metal oxides and semiconductor fine particles. Examples of the metal oxides include oxides of Fe, Co, Ni, Cu, Ag, Au, Zn, Cd, Hg, Al, Ga, In, Tl, Si, Ge, Sn, Pb, Ti, Zr, Mn, Eu, Y, Nb, Ce, Ba, and the like. Examples of the metal oxides include $Fe_3O_4$, $Fe_2O_3$, $Co_3O_4$, $ZrO_2$, $CeO_2$, $BaO \cdot 6Fe_2O_3$, $SiO_2$, $TiO_2$, $ZnO_2$, $SnO_2$, $Al_2O_3$, $MnO_2$, $NiO$, $Eu_2O_3$, $Y_2O_3$, $Nb_2O_3$, $InO$, $ZnO$, $Al_5(Y+Tb)_3O_{12}$, $BaTiO_3$, $LiCoO_2$, $LiMn_2O_4$, $K_2O \cdot 6TiO_2$, $AlOOH$, and the like.

Of these metal oxides, for example, $\gamma$-$Fe_2O_3$, $Fe_3O_4$, and $MgFe_2O_3$ are useful for MRI and magneto hyperthermia therapy because of their ferromagnetic properties. For example, $GdVO_4$, :Re and $BaSnO_3$ are useful for fluorescent imaging because these have light emitting characteristics. For example, $Gd(OH)_3$ and $GdVO_4$, :Re are useful for neutron capture therapy, because these have large neutron capture cross sections. Examples of the semiconductor fine particles include CdS, CdSe, and the like. CdS and CdSe are useful for fluorescent imaging.

The metal simple substance is not particularly limited, as long as nanoparticles can be formed. Examples of the metal simple substance include Fe, Co, and Au. Fe and Co are useful for MRI and magnetic manipulator, and Au is useful as a probe for X-ray imaging.

The modification of the metal simple substance or the metal compound with the RolA protein can be conducted by causing a RolA protein to adsorb onto a metal simple substance or a metal compound as described in Examples.

A ligand which provides an immune-response evasion function may be bound to the metal simple substance or the metal compound. The ligand may be selected from ligands known as candidate compounds in the field, or may be selected from ligands obtained from animals including human, plants, or microorganisms and known to have the above-described immune-response evasion function or expected to have the above-described immune-response evasion function. Regarding typical ligand molecules, water-soluble ones can be used, and examples thereof include phenols and derivatives thereof. More specifically, the ligand may be catechol, a derivative thereof, or the like, and examples thereof include compounds having the general formula (1):

[Chem. 1]

(1)

[In the formula, one R or multiple Rs, which may be the same or different, may be present, and each represent a group selected from the group consisting of hydrogen, alkyl groups, a hydroxy group, a nitro group, carboxyalkyl groups, carboalkoxyalkyl groups, hydroxyalkyl groups, cyanoalkyl groups, and acylaminoalkyl groups].

In the above-described formula (1), the alkyl group represented by R may be a linear or branched lower alkyl group having 1 to 5 carbon atoms or a linear or branched higher alkyl group having more carbon atoms, and is preferably a lower alkyl group having 1 to 5 carbon atoms. Examples of the lower alkyl groups include a methyl group, an ethyl group, a n-propyl group, an i-propyl group, a n-butyl group, a sec-butyl group, an isobutyl group, a tert-butyl group, a n-pentyl group, a neo-pentyl group, and the like, and, for example, a methyl group, an ethyl group, and the like are preferable. Examples of the higher alkyl group include a n-hexyl group, a 2-methyl-1-butyl group, a 3-methyl-1-butyl group, a 2-methyl-2-butyl group, a 3-methyl-2-butyl group, a 2,2-dimethyl-1-propyl group, a 4-methyl-1-pentyl group, a 3-ethyl-3-pentyl group, and the like. Examples of the alkoxy group of the carboalkoxy moiety in the carboalkoxyalkyl group represented by R include a methoxy group, an ethoxy group, a n-propoxy group, an i-propoxy group, a n-butoxy group, a sec-butoxy group, an isobutoxy group, a tert-butoxy group, and the like, and may further include alkoxy groups in which one or multiple substituents selected from the group consisting of halogen groups, a hydroxy group, a carboxy group, carboalkoxy groups, a phenyl group, a p-nitrophenyl group, and the like are further introduced to the alkyl moieties of the alkoxy groups. Examples of the acyl group represented by R include acyl groups derived from carboxylic acids, and examples of the carboxylic acids include formic acid, acetic acid, propionic acid, butyric acid, valeric acid, oxalic acid, succinic acid, malonic acid, benzoic acid, phthalic acid, terephthalic acid, lactic acid, malic acid, fumaric acid, maleic acid, amino acids, amino acids (for example, naturally occurring amino acids), and the like.

Regarding a typical ligand molecule, 3,4-dihydroxycinnamic acid (DHCA) can be used.

[Chem. 2]

(2)

DHCA is extracted from some kinds of fruits and vegetables, and considered to be a molecule having no toxicity (S. Kim, S. Bok, S. Lee, H. Kim, M. Lee, Y. B. Park, M. Choi, Toxycol. Appl. Pharmacol. 2005, 208, 29-36).

The nanoparticles of the metal simple substance or the metal compound to which the ligand providing the immune-response evasion function is bound can be synthesized by subjecting a nanoparticle precursor solution containing a metal salt containing metal ions etc., serving as a nanoparticle source, and the like to a reaction treatment in the presence of ligand molecules, which provide the immune-response evasion function, under a high-temperature and high-pressure water environment, for example, in subcritical water or supercritical water.

The composition of the present invention is particularly suitable for biomedical applications, for example, uses in the biological field and the medical field. The composition can be expected to be efficiently delivered to a target tissue or a target cell, without being captured by the immune system of an animal. Moreover, to the RolA protein modifying the surface, for example, an antibody which specifically recognizes a specific tumor cell or a specific target cell, or the like can be bound, or moreover a specific physiologically active substance (a cytokine, a chemokine, a cytotoxic factor, a anti-cancer factor, a cytotoxic factor, an antibiotic, or the like), annexin V which recognizes apoptosis cells, or the like can be bound.

The bonding of a specific antibody or a physiologically active substance to the RolA protein can be achieved by a gene fusion method, or by adsorption by the protein-protein interaction (Takahashi T. et al., Mol. Microbiol. 2005, 57, 1780-1798).

Thus obtained composition is useful as target-directed nanoparticles, and is useful as reagents for research and development, diagnostic agents, therapeutic agents, and the like for target tissue imaging, magneto hyperthermia therapy, neutron capture therapy, fluorescent imaging, and the like in human, animals, and the like. In addition, a high-performance imaging probe can be achieved by the composition in a small administration amount (microdose). Moreover, when a target-directed factor is bound, the composition becomes useful for development of new methods for diagnosing or treating cancer or arteriosclerosis, and hence can be applied to drug development.

In addition, the composition of the present invention is expected to achieve high targeted-delivery performance, and hence is preferably useful in the biological field and the medical field, for example, for cell sorting, cell labeling agents, nanoparticles for medical applications including drug delivery system (DDS) and the like, agents for tumor hyperthermia therapy, iron supplements, X-ray contrast agents, MRI contrast agents, blood vessel contrast agents, lymph node contrast agents, and blood flow measurement, and further as a carrier for locally and intensively administrating a drug by using a magnetic field and/or for collecting or removing a biological material, and the like.

Moreover, the composition of the present invention can be used as a coating agent for implanted devices and the like, so that the affinity for living organisms of the implanted devices and the like can be increased.

EXAMPLES

Hereinafter, the present invention will be described more specifically based on Examples. However, the present invention is not limited to Examples below.

Example 1

Response of Myeloid Dendritic Cells to RolA

To verify that RolA has an immunity evasion function, an immunostimulation activity on myeloid dendritic cells was investigated by using a purified RolA. If RolA has an immune-response evasion function, no cytokines should be secreted even when the RolA is introduced into myeloid dendritic cells. In this respect, a RolA was introduced into myeloid dendritic cells, and the amount of a cytokine produced was quantitatively determined.

(1) Purification of RolA from RolA Over-Expressing Koji Mold pNEN142-AorolA was constructed by inserting ORF (see SEQ ID NO: 1) of RolA into pNEN142 vector (Tsuboi, H. et al. Biosci. Biotechnol. Biochem. 2005, 69(1), 206-208), which is an *A. oryzae* over-expression vector. *A. oryzae* RolA over-expression strain (hereinafter, referred to as "enoA142-RolA") obtained by introducing the vector into an *A. oryzae* NSlD-tApEnBdlVdV strain (Yoon J. et al. Appl Microbiol Biotechnol. 2009, 82, 691-701) was used in Examples.

Purification of RolA was conducted by modifying the method reported by Takahashi et al. (Takahashi T. et al., Mol. Microbiol., 2005, 57, 1780-1798) as follows.

To three 1 L baffled Erlenmeyer flasks containing 400 ml of YPM liquid culture medium, spores of the RolA over-expression strain were seeded at $1 \times 10^6$ spores/ml, and cultured with shaking at 30° C. for 24 hours. The culture liquid was filtered through Miracloth (CALBIOCHEM) to remove the fungus bodies. Thus, a culture supernatant was obtained. To the culture supernatant, ammonium sulfate was added to achieve 40% saturation, and a supernatant fraction was obtained by centrifugation at 8,000×g and 4° C. for 30 minutes. The supernatant fraction was subjected to Phenyl-Sepharose CL-4B (GE Healthcare) equilibrated with 10 mM Tris-HCl buffer (pH 8.0) in which ammonium sulfate was dissolved at 40% saturation. The adsorbed fraction was eluted with a linear gradient of 40-0% saturated ammonium sulfate. All the eluted fractions were subjected to SDS-PAGE, and the fraction of the band detected at a position of 13.6 kDa, which is an estimated molecular mass of RolA, was collected. The collected fraction was dialyzed by using 5 mM Tris-HCl buffer (pH 9.0), and subjected to Cellulofine Q-500 (SEIKAGAKU CORPORATION) equilibrated with the same buffer solution. The adsorbed fraction was eluted by a linear gradient of 0-0.4 M NaCl, and all the eluted fractions were subjected to SDS-PAGE. The fraction of the band detected at a position of 13.6 kDa, which is an estimated molecular mass of RolA, was collected. Subsequently, the collected fraction was dialyzed by using 10 mM citric acid-NaOH buffer (pH 4.0), and subjected to SP-Sepharose FF (GE Healthcare) equilibrated with the same buffer solution. The adsorbed fraction was eluted by a linear gradient of 0-0.3 M NaCl, and all the eluted fractions were subjected to SDS-PAGE. The fraction of the band detected at a position of 13.6 kDa, which is an estimated molecular mass of RolA, was collected. The collected fraction was dialyzed against purified water and then freeze-dried. The freeze-dried purified RolA was re-dissolved in a buffer solution, as appropriate, before use.

(2) LPS Removal from Purified RolA Solution

When a protein is introduced in a cell experiment, the contamination with LPS may lead to expression of cytotoxicity or decrease in the efficiency of the introduction of the protein. In this respect, LPS was removed from the purified RolA solution.

For the LPS removal, a polymyxin-immobilized column (Detoxi-GelEndotoxinRemovingGel, Thermo SCIENTIFIC) was used. In addition, for the buffer solution, The Japanese Pharmacopoeia Otsuka distilled water for injection (Otsuka Pharmaceutical Co., Ltd.) was used. The glass apparatuses used were dry-heat-sterilized at 250° C. for 2 hours.

All operations were conducted in a clean bench. A polymyxin-immobilized column (bed volume: 1 ml) was washed with 5 ml of 1% sodium deoxycholate. Next, the sodium deoxycholate was removed with 10 ml of The Japanese Pharmacopoeia Otsuka distilled water for injection, and the column was equilibrated with 5 ml of Dulbecco's PBS (−) (NISSUI PHARMACEUTICAL CO., LTD.). The purified RolA solution was subjected to the column, and incubated at room temperature for 1 hour. After that, elution with Dulbecco's PBS(−) was carried out, and the amount of LPS contained in the purified RolA solution after the elution was quantitatively determined by the colorimetric method using a LAL (*Limulus Amebocyte* Lysate) reagent (Seikagaku Biobusiness Corporation).

(3) Quantification of LPS in Purified RolA Solution

The LAL reagent used was Endospecy ES-24S (Seikagaku Biobusiness Corporation), and the diazo coupling solution used was Toxicolor DIA set (Seikagaku Biobusiness Corporation). In addition, an endotoxin standard from *E. coli* strain 0113:H10 (Seikagaku Biobusiness Corporation) was used.

By the colorimetric method using the LAL reagent, the quantification of LPS was conducted. To each vial containing the LAL reagent, 200 µl of a buffer solution was added, followed by stirring for 2 seconds. Next, 200 µl of one of the purified RolA solution, LPS standard solutions (a dilution series), and a blank solution was added to each vial, followed by stirring for 1 second and by incubation at 37° C. for 30 minutes. After the incubation, the vials were placed on ice, and 500 µl of each of a HCl solution in which sodium nitrite was dissolved at 0.04%, a 0.3% ammonium sulfamate solution, and a 0.07% N-(1-naphthyl)ethylenediamine dihydrochloride solution was added in this order to the vial (after addition of each solution, stirring for 2 seconds was conducted). After that, the absorbance was measured at a wavelength of 545 nm, and the amount of LPS contained in the purified RolA solution was calculated from the absorbance.

Figure 1:
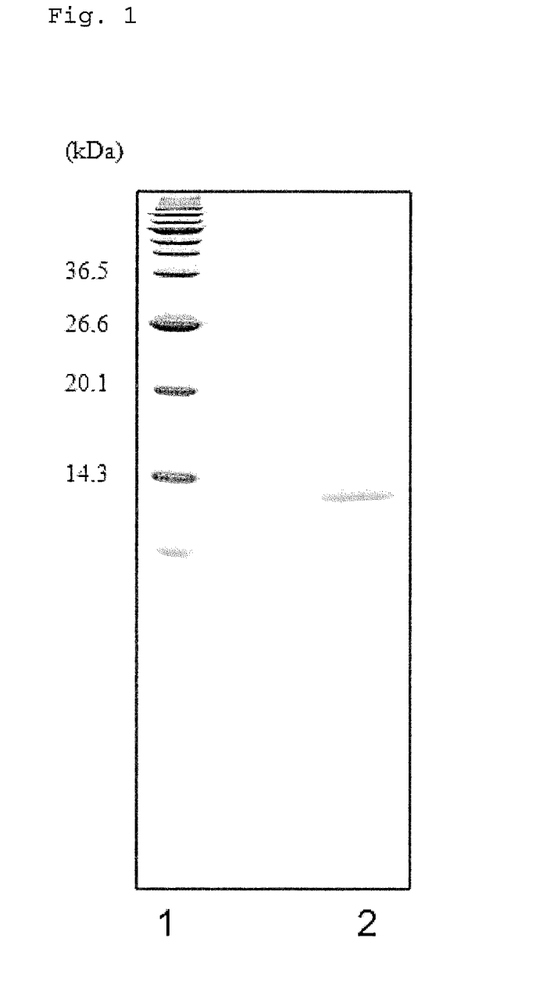
FIG. 1 is an electrophoretogram showing a result of SDS-PAGE (SDS-polyacrylamide gel electrophoresis) analysis of a purified RolA from which LPS was removed. In the photograph, molecular weight markers were electrophoresed in Lane 1, and the purified RolA was electrophoresed in Lane 2.

The results were that the LPS concentration in the purified RolA solution (protein concentration: 526.3 µg/ml) was 26.7 ng/ml before the polymyxin-immobilized column treatment, whereas the LPS concentration in the purified RolA solution (protein concentration: 333.0 pg/ml) was 0.210 ng/ml after the column treatment (FIG. 1). When dendritic cells are stimulated by using 50 µg/ml RolA, 32 µg/ml of LPS is included. However, it is conceivable that the LPS at this concentration does not affect the cytotoxicity and the protein introduction efficiency. From these results, the LPS concentration was successfully reduced to a concentration usable in a cell experiment by the treatment of the purified RolA solution with the polymyxin-immobilized column.

(4) Quantification of IL-12 Produced by Myeloid Dendritic Cells

The amount of IL-12, which is a cytokine, produced was quantified to investigate the immune-response evasion function of the RolA.

First, C57BL/6 mouse myelocytes were cultured for 8 to 9 days in 10% FCS/RPMI 1640 culture medium supplemented with GM-CSF (20 ng/ml) to prepare myeloid dendritic cells. Subsequently, the obtained cells were cultured together with RolA for 24 hours, and the IL-12 concentration in the culture supernatant was measured by the ELISA method.

Figure 2:
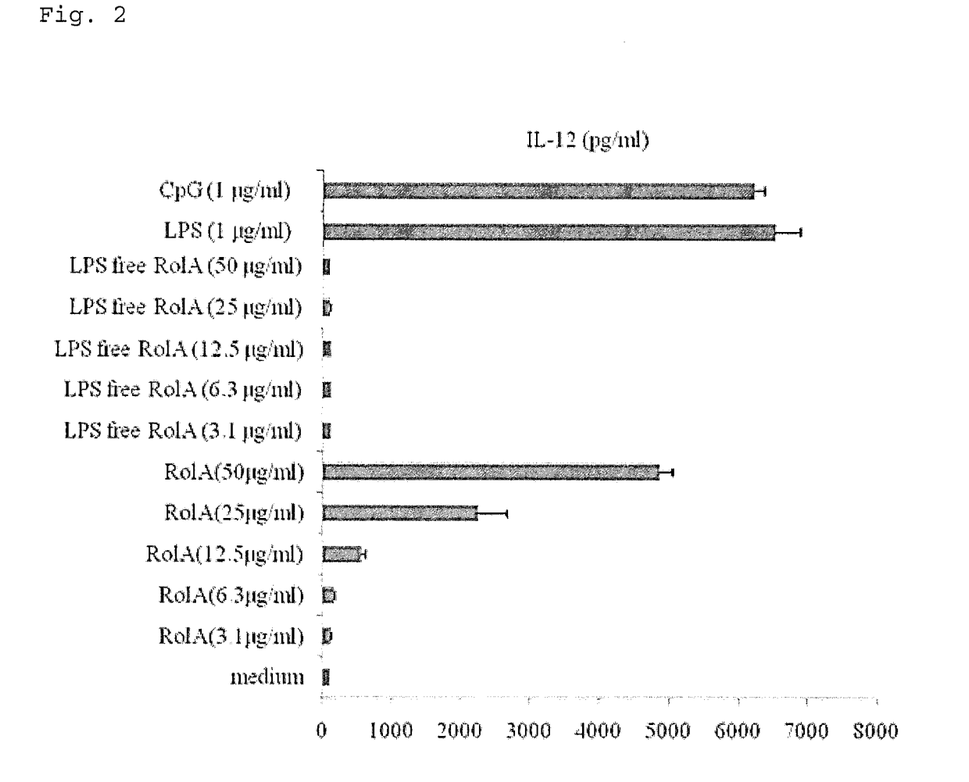
FIG. 2 is a graph showing results of quantification of IL-12 (interleukin-12) production by myeloid dendritic cells. To the myeloid dendritic cells, a RolA from which LPS (Lipopolysaccharide) was removed or the RolA from which LPS was not removed was introduced. In addition, LPS and CpG were used as controls.

The result was that no IL-12 was detected when the RolA was introduced into the myeloid dendritic cells (FIG. 2). This has shown that the RolA has an immune-response evasion function on the myeloid dendritic cells.

Example 2

Preparation of RolA-Coated $Fe_3O_4$ Nanoclusters

Now that the RolA was confirmed to have an immune-response evasion function, stealth particles, which were fine particles coated with the RolA, were prepared. As the fine particles to be coated with the RolA, catechol-modified $Fe_3O_4$ nanoclusters, which were functional nanoparticles for medical applications, having a diameter of 200 nm were used.

(1) Preparation of $Fe_3O_4$ Nanoclusters

Equal volumes of 800 mM aqueous DHCA solution and 400 mM aqueous $FeSO_4$ solution were mixed with each other, and then the pH was adjusted to 9.5 by adding 5 N KOH dropwise. Subsequently, purified water was added to adjust the concentrations of DHCA and $FeSO_4$ to 200 mM and 100 mM, respectively. To a batch-type metal reactor (SUS316, internal volume: 5.0 mL), 4.35 mL of the adjusted solution was sealed, and the temperature was raised to 250° C. by using an electric furnace. Sixty minutes later, the reactor was taken out, and the reaction was stopped by cooling with water. The product was recovered by centrifugation, and then washed by repeating redispersion of the product in a 0.01M aqueous KOH solution and centrifugation three times. After the washing, the product was dispersed in purified water.

The prepared catechol-modified $Fe_3O_4$ nanoclusters (hereinafter, referred to as "$Fe_3O_4$ nanoclusters") having a diameter of 200 nm cannot evade phagocytosis by macrophages.

Hereinafter, the particles were coated with the RolA, and immunostimulation on dendritic cells and an effect on the phagocytosis by macrophages were investigated.

(2) Saturation Amount of RolA Bound to $Fe_3O_4$ Nanoclusters

The $Fe_3O_4$ nanoclusters were used as fine particles, and the purified RolA was used as RolA. This measurement was conducted based on a method for adsorbing RolA onto Teflon fine particles. Each of 2 to 5 µg portions of the purified RolA was dissolved in 5 mM MES-NaOH buffer (pH 5.0) containing $Fe_3O_4$ nanoclusters (685.125 mm$^2$ in terms of surface area) (total amount: 100 µl), and an adsorption reaction was allowed to proceed at 30° C. for 10 minutes. Then, the $Fe_3O_4$ nanoclusters were recovered by centrifugation at 4° C. and 17,300×g for 10 minutes. The precipitated $Fe_3O_4$ nanoclusters were washed by adding 5 mM MES-NaOH buffer (pH 5.0), and then the $Fe_3O_4$ nanoclusters were recovered again by centrifugation at 4° C. and 17,300×g for 10 minutes. To this, SDS-sample buffer was added to denature the RolA adsorbed on the $Fe_3O_4$ nanoclusters with SDS, and the $Fe_3O_4$ nanoclusters adsorbing the RolA were directly subjected to SDS-PAGE. Here, 1 to 4 µg portions of RolA were simultaneously subjected to the SDS-PAGE for quantification. ACBB (coomassie brilliant blue) staining reagent of BEX-CEL was used, and the band intensity was converted into a numeric value with Image J, and the amount was determined.

Figure 3:
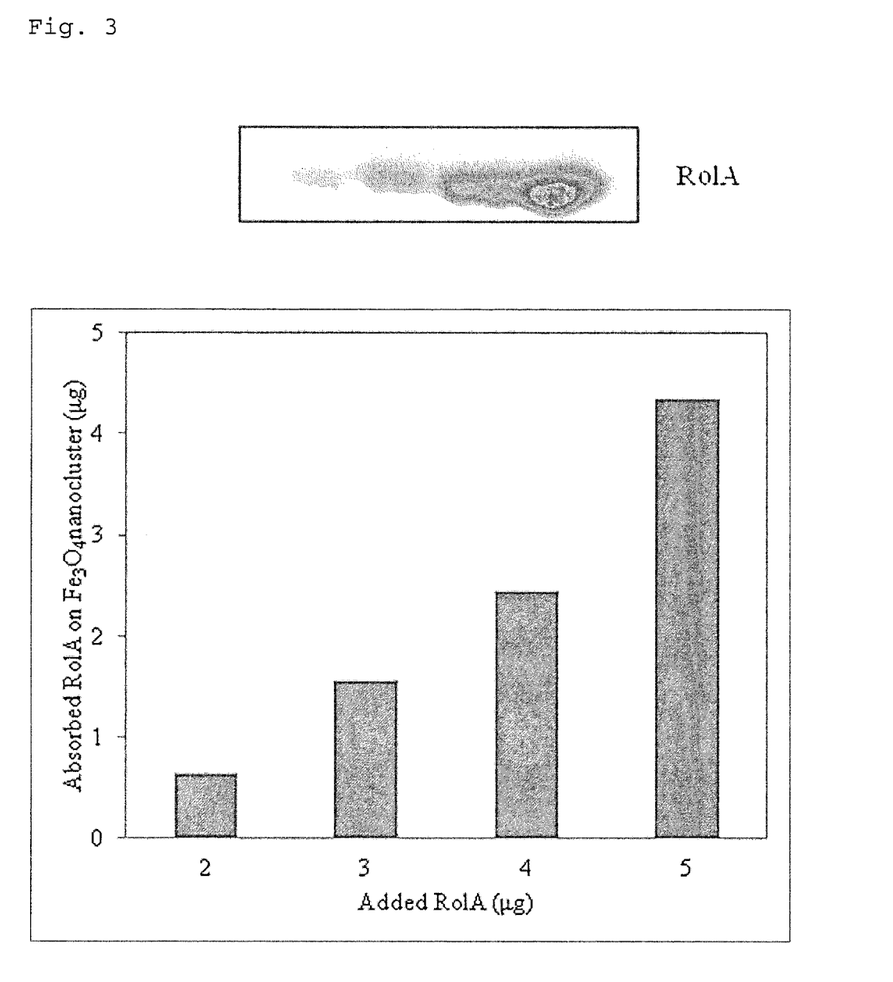
FIG. 3 is a graph showing results of quantification of the RolA adsorbed on catechol-modified $Fe_3O_4$ nanoclusters.

The results were as follows: the amounts of the RolA adsorbed on the $Fe_3O_4$ nanoclusters were 0.6 µg in a case where 2 µg of the RolA was added, 1.6 µg in a case where 3 µg of the RolA was added, 2.4 µg in a case where 4 µg of the RolA was added, and 4.3 µg in a case where 5 µg of the RolA was added (FIG. 3). Based on a calculation, it is know that adsorption of 1.6 µg of RolA is required for completely coating $Fe_3O_4$ nanoclusters having a surface area of 685.125 mm$^2$. Hence, it has been found that the $Fe_3O_4$ nanoclusters can be completely coated by adding 3 µg of the RolA.

(3) Preparation of RolA-Coated $Fe_3O_4$ Nanoclusters

Fine particles used were the $Fe_3O_4$ nanoclusters, and RolA used was the purified RolA from which LPS was removed. In addition, tempered and hard glass sample tubes sterilized by dry heating at 250° C. for 2 hours were used. The buffer solutions used were all prepared by using The Japanese Pharmacopoeia Otsuka distilled water for injection (Otsuka Pharmaceutical Co., Ltd.).

3 µg of the purified RolA from which LPS was removed was dissolved in a 5 mM MES-NaOH buffer (pH 5.0) containing $Fe_3O_4$ nanoclusters (685.125 mm$^2$ in terms of surface area) (total amount: 100 µl), and an adsorption reaction was allowed to proceed at 30° C. for 10 minutes. Then, the $Fe_3O_4$ nanoclusters were recovered by centrifugation at 4° C. and 6,300×g for 10 minutes. The precipitated $Fe_3O_4$ nanoclusters were washed by adding 5 mM MES-NaOH buffer (pH 5.0), and then the $Fe_3O_4$ nanoclusters were recovered again by centrifugation at 4° C. and 6,300×g for 10 minutes. To this precipitates, 62.5 µl of Dulbecco's PBS(−) was added, and the precipitates were suspended. Thus, RolA-coated $Fe_3O_4$ nanoclusters were obtained.

Example 3

Response of Myeloid Dendritic Cells to RolA-Coated $Fe_3O_4$ Nanoclusters

The immunostimulation activity on myeloid dendritic cells was investigated by using the prepared RolA-coated $Fe_3O_4$ nanoclusters. If the RolA in the state of being adsorbed on the $Fe_3O_4$ nanoclusters has an immune-response evasion function, no cytokines should be secreted when the RolA-coated $Fe_3O_4$ nanoclusters are introduced into myeloid dendritic cells. In this respect, the RolA-coated $Fe_3O_4$ nanoclusters were introduced into myeloid dendritic cells, and the amounts of cytokines produced were quantified.

(1) Quantification of IL-12 Produced by Myeloid Dendritic Cells

The amount of IL-12, which is a cytokine, produced was quantified to investigate the immune-response evasion function of the RolA-coated $Fe_3O_4$ nanoclusters.

First, C57BL/6 mouse myelocytes were cultured for 8 to 9 days in 10% FCS/RPMI 1640 culture medium supplemented with GM-CSF (20 ng/ml). Thus, myeloid dendritic cells were prepared. The obtained cells were cultured together with the RolA-coated $Fe_3O_4$ nanoclusters for 24 hours, and the concentration of IL-12 in the culture supernatant was measured by the ELISA method.

Figure 4:
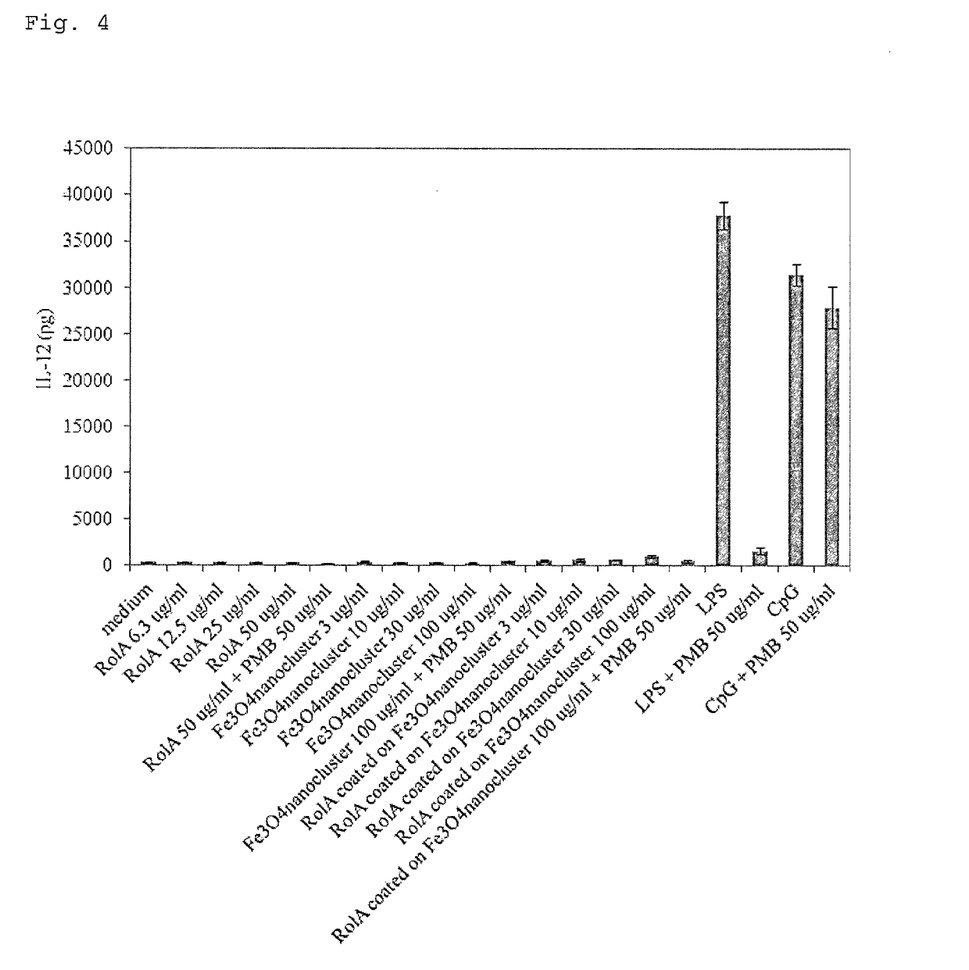
FIG. 4 is a graph showing results of quantification of IL-12 production by myeloid dendritic cells. To the myeloid dendritic cells, the RolA, RolA-free $Fe_3O_4$ nanoclusters, or RolA-coated $Fe_3O_4$ nanoclusters were introduced. LPS and CpG were used as controls.

The result was that no IL-12 was detected when the RolA-coated $Fe_3O_4$ nanoclusters were introduced into the myeloid dendritic cells (FIG. 4). Also in a case where RolA-free $Fe_3O_4$ nanoclusters were introduced, no IL-12 was detected. These results indicate that the immune response evasion activity of the RolA was effective even in a state where the RolA was adsorbed onto the $Fe_3O_4$ nanoclusters.

(2) Quantification of TNF-α Produced by Myeloid Dendritic Cells

The amount of TNF-α, which is a cytokine, produced was quantified to investigate an immune response evasion activity of the RolA-coated $Fe_3O_4$ nanoclusters.

First, C57BL/6 mouse myelocytes were cultured for 8 to 9 days in 10% FCS/RPMI 1640 culture medium supplemented with GM-CSF (20 ng/ml). Thus, myeloid dendritic cells were prepared. The obtained cells were cultured for 24 hours together with the RolA-coated $Fe_3O_4$ nanoclusters, and the concentration of TNF-α in the culture supernatant was measured by the ELISA method.

Figure 5:
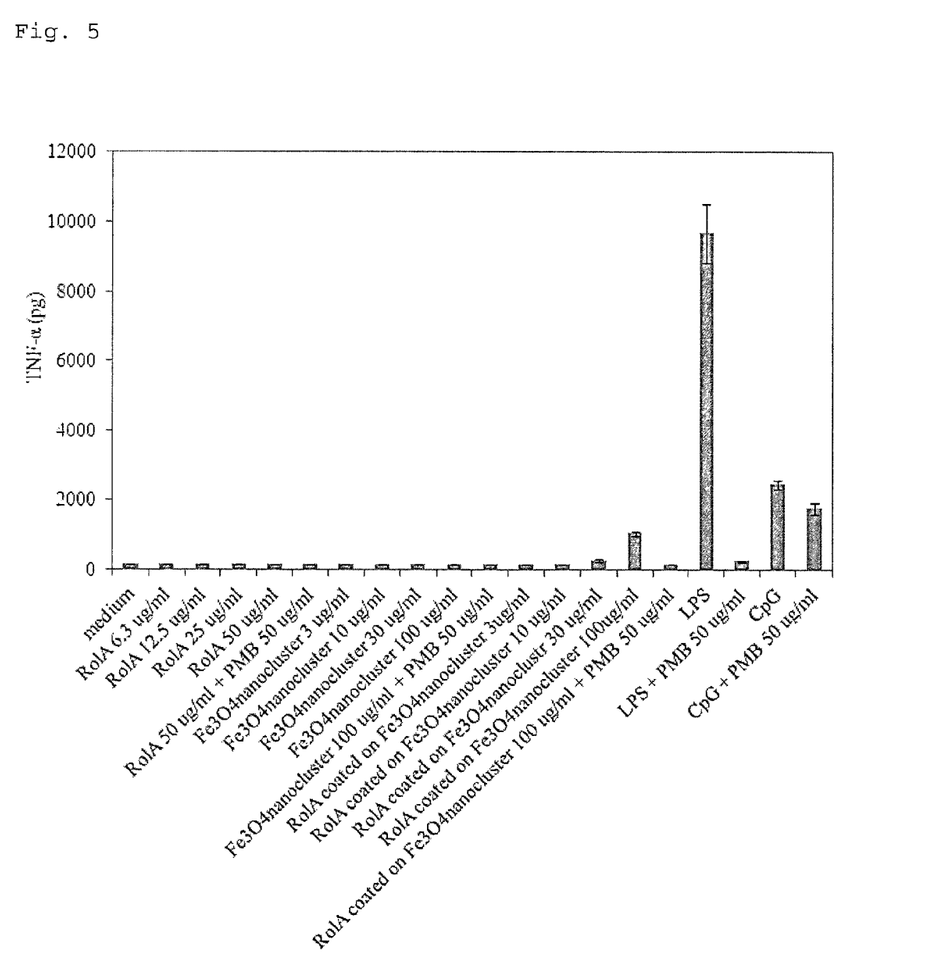
FIG. 5 is a graph showing results of quantification of TNF-α (tumor necrosis factor-α) production by myeloid dendritic cells to which the RolA-coated $Fe_3O_4$ nanoclusters were introduced. In addition, the same quantification was conducted by using the RolA and the RolA-free $Fe_3O_4$ nanoclusters. LPS and CpG were used as controls.

The result was that no TNF-α was detected when the RolA, the $Fe_3O_4$ nanoclusters, and the RolA-coated $Fe_3O_4$ nanoclusters were introduced into the myeloid dendritic cells (FIG. 5). These results showed that the immune response evasion activity of the RolA was effective even when the RolA was adsorbed onto the $Fe_3O_4$ nanoclusters.

Example 4

Response of Macrophages to RolA-Coated $Fe_3O_4$ Nanoclusters (1) Macrophages Phagocytosis Experiment Using Confocal Microscope The immune response evasion activities of the RolA have been demonstrated by Example 3 from the viewpoints of both the IL-12 production and the TNF-α production. Next, an immune response evasion activity of the RolA on macrophages was investigated. If the immune response evasion activity of RolA is effective also in a state where the RolA is adsorbed on the $Fe_3O_4$ nanoclusters, the RolA-coated $Fe_3O_4$ nanoclusters should undergo reduced phagocytosis by macrophages. In this respect, LAMP1 (lysosome-associated membrane protein type 1), which is a lysosome-associated membrane protein of macrophages, was immunostained, and colocalization with the $Fe_3O_4$ nanoclusters was observed using a confocal microscope to investigate the phagocytosis of the $Fe_3O_4$ nanoclusters by macrophages.

RAW264.7 cells were prepared at $2 \times 10^5$ cells/ml, and 500 μl of the cells was seeded into an 8-well chamber slide, and incubated for 24 hours. To 1 ml of 10% FCS/RPMI, 9.2 μl of 1.8 mg/ml $Fe_3O_4$ nanocluster emulsion was added, and 268 μl thereof was added to the chamber slide from which the supernatant had been removed, and the chamber slide was incubated for 1 hour. Using Cytofix/Cytoperm, the cells were stained with Alexa Fluor 488-conjugated anti-mouse LAMP-1 antibody. In addition, DAPI staining was also conducted.

Figure 6:
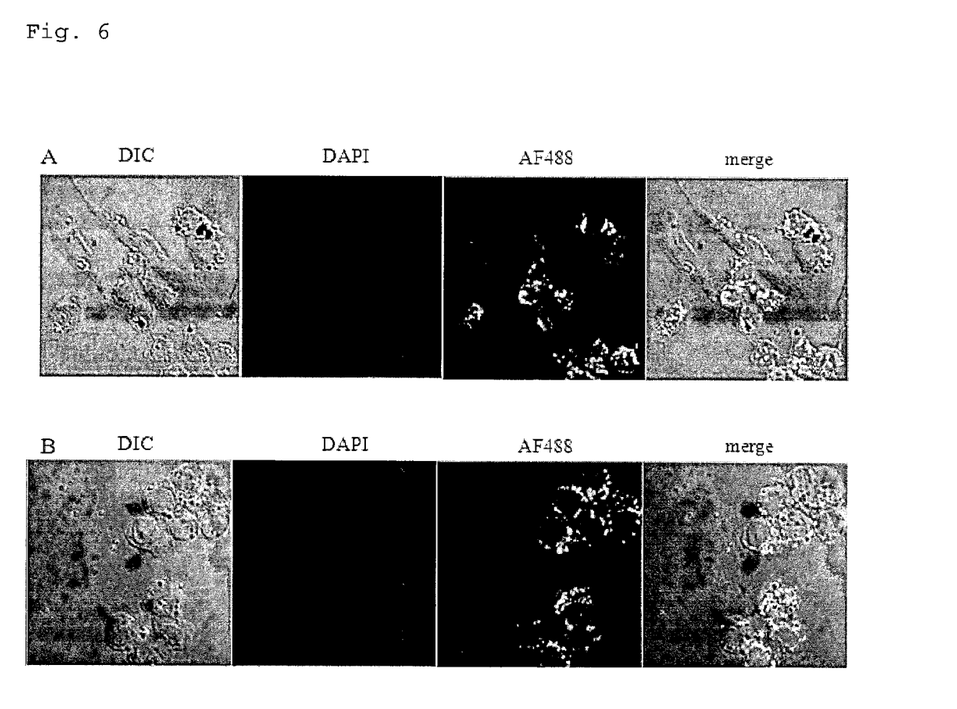
FIG. 6 shows micrographs showing results of observation of colocalization of macrophages and $Fe_3O_4$ nanoclusters using a confocal fluorescence microscope. Part A shows an observation result of phagocytosis of the RolA-free $Fe_3O_4$ nanoclusters by RAW264.7 cells. Part B shows an observation result of phagocytosis of the RolA-coated $Fe_3O_4$ nanoclusters by RAW264.7 cells.

The results were that, as compared with the $Fe_3O_4$ nanoclusters, the RolA-coated $Fe_3O_4$ nanoclusters caused less morphological change of the macrophages, and tended to undergo reduced phagocytosis (FIG. 6).

(2) Macrophages Phagocytosis Experiment Using Atmospheric Scanning Electron Microscope By using an atmospheric scanning electron microscope (JEOL Ltd.), phagocytosis of the $Fe_3O_4$ nanoclusters by macrophages was observed with a high resolution.

RAW264.7 cell were seeded into atmospheric scanning electron microscope dishes at $2 \times 10^5$ cells/dish, and were incubated for 24 hours. To 1980 μl of 10% FCS/RPMI, 20 μl of 5.5 mg/ml $Fe_3O_4$ nanocluster emulsion was added, and 2 ml thereof was added to the dishes from which the supernatants were removed, and the dishes were incubated for 1 hour. The cells were treated with glutaraldehyde or 4% PFA for 15 minutes for fixation, and then observed with the atmospheric scanning electron microscope.

Figure 7:
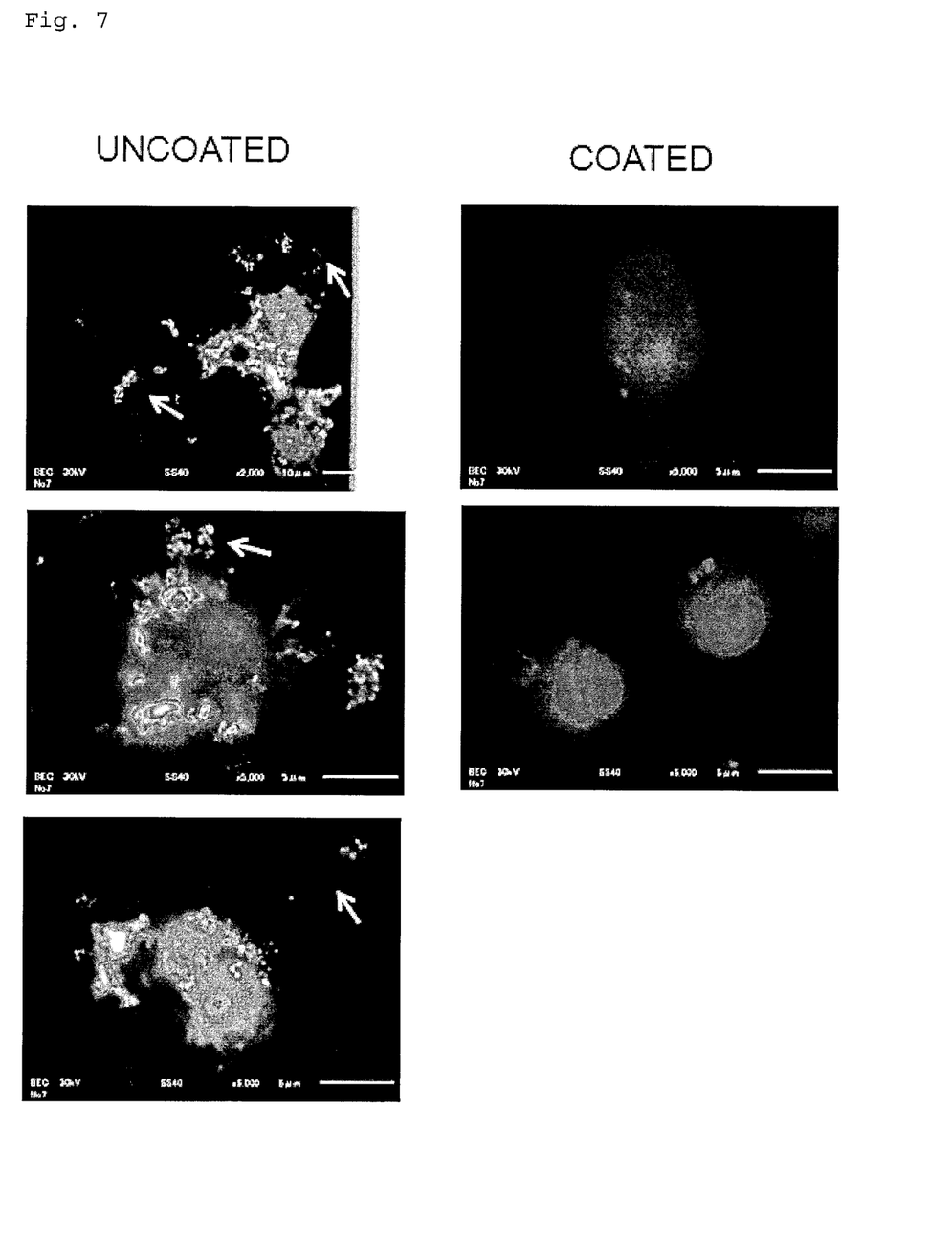
FIG. 7 shows micrographs showing results of observation of colocalization of RAW264.7 cells and $Fe_3O_4$ nanoclusters using an atmospheric scanning electron microscope. The left photographs show observation results of phagocytosis of the RolA-free $Fe_3O_4$ nanoclusters by the RAW264.7 cells, and the right photographs show observation results of phagocytosis of the RolA-coated $Fe_3O_4$ nanoclusters by the RAW264.7 cells. The arrows in the left photographs indicate that phagocytosis by RAW264.7 cells occurred.

The results were that, as compared with the $Fe_3O_4$ nanoclusters, the RolA-coated $Fe_3O_4$ nanoclusters caused less morphological change of the macrophages, and tended to lead to a reduced phagocytic ability (FIG. 7).

From the above-described results, it has been demonstrated that the RolA-coated $Fe_3O_4$ nanoclusters do not cause immunostimulation on dendritic cells, and can evade the phagocytosis by macrophages.

INDUSTRIAL APPLICABILITY

As described above, the composition of the present invention, which is nanoparticles coated with a RolA protein, has excellent immune-response evasion functions (stealth functions), and is highly safe to living organisms. Hence, the composition of the present invention is extremely useful as, for example, stealth nanoparticles for small-animal imaging in treatment method development, as well as stealth nanoparticles for diagnosing or treating human, and further a coating agent for implanted devices.

The invention claimed is:

1. A composition for avoiding immunostimulation on a dendritic cell and evading phagocytosis by a macrophage, comprising a nanometer-sized metal simple substance or a nanometer-sized metal compound whose surface is modified with a RolA protein.

2. The composition according to claim 1, wherein the RolA protein is originated from a filamentous fungus of the genus *Aspergillus*.

3. The composition according to claim 1, wherein the nanometer-sized metal simple substance or the nanometer-sized metal compound is modified with 3,4-dihydroxyhydrocinnamic acid.

4. The composition according to claim 2, wherein the nanometer-sized metal simple substance or the nanometer-sized metal compound is modified with 3,4-dihydroxyhydrocinnamic acid.

5. The composition according to claim 1, wherein the nanometer-sized metal simple substance or the nanometer-sized metal compound is $Fe_3O_4$.

6. The composition according to claim 2, wherein the nanometer-sized metal simple substance or the nanometer-sized metal compound is $Fe_3O_4$.

7. The composition according to claim 3, wherein the nanometer-sized metal simple substance or the nanometer-sized metal compound is $Fe_3O_4$.

8. The composition according to claim 4, wherein the nanometer-sized metal simple substance or the nanometer-sized metal compound is $Fe_3O_4$.

* * * * *